United States Patent [19]

Pivawer et al.

[11] 3,979,403

[45] Sept. 7, 1976

[54] PROCESS FOR THE PREPARATION OF 3-TRICHLOROMETHYL-5-CHLORO-1,2,4-THIADIAZOLE

[75] Inventors: Philip M. Pivawer, Hamden; Douglas A. Farmer, Jr., West Haven, both of Conn.

[73] Assignee: Olin Corporation, New Haven, Conn.

[22] Filed: Mar. 31, 1975

[21] Appl. No.: 561,765

Related U.S. Application Data

[63] Continuation-in-part of Ser. No. 465,773, May 1, 1974, abandoned.

[52] U.S. Cl. .................. 260/302 D; 260/453 R
[51] Int. Cl.² ........................ C07D 285/08
[58] Field of Search .................. 260/302 D

[56] References Cited

UNITED STATES PATENTS 3,260,725  7/1966  Schroeder .................. 260/302 D

*Primary Examiner*—Nicholas S. Rizzo
*Assistant Examiner*—Diana G. Rivers
*Attorney, Agent, or Firm*—Thomas P. O'Day; F. A. Iskander

[57] ABSTRACT

A process is provided for preparing 3-trichloromethyl-5-chloro-1,2,4-thiadiazole in improved yields by reacting a defined molar excess trichloroacetamidine with trichloromethanesulfenyl chloride while controlling pH of the reaction mixture. The present process may advantageously be employed in a batch or continuous process.

10 Claims, No Drawings

PROCESS FOR THE PREPARATION OF 3-TRICHLOROMETHYL-5-CHLORO-1,2,4-THIADIAZOLE

RELATED APPLICATIONS

This is a continuation-in-part of co-pending application Ser. No. 465,773 filed May 1, 1974, now abandoned.

BACKGROUND OF THE INVENTION

The present invention relates to an improved process for producing 3-trichloromethyl-5-chloro-1,2,4-thiadiazole. 3-Trichloromethyl-5-chloro-1,2,4-thiadiazole and its derivatives are biocides which are effective against fungi, nematodes and in controlling weeds. It and its derivatives are particularly effective as soil fungicides which function in the soil to protect seeds and growing plants against such pathogenic fungi as Pythium, Fusarium, Rhizoctonia, and Sclerotium. More important, 3-trichloromethyl-5-chloro-1,2,4-thiadiazole is an intermediate in the manufacture of compounds disclosed in Schroeder, U.S. Pat. No. 3,260,725 including but not limited to 3-trichloromethyl-5-ethoxy-1,2,4-thiadiazole.

As disclosed in U.S. Pat. Nos. 3,260,725 and 3,260,588 it is known to prepare 3-trichloromethyl-5-chloro-1,2,4-thiadiazole by adding aqueous caustic to a mixture containing approximately equimolar amounts of trichloroacetamidine hydrochloride and trichloromethanesulfenyl chloride in methylene chloride. Utilizing this procedure yields of 56% are obtained. More recently 3-trichloromethyl-5-chloro-1,2,4-thiadiazole has been prepared by adding excess trichloromethane sulfenyl chloride to a solution of not more than 11% by weight trichloroacetamidine in an organic solvent such as methylene chloride at a temperature of −5°C. to 10°C. followed by addition of caustic at 0°–20°C. to effect ring closure. The solvent is then evaporated and the residue distilled to recover the desired product in yields of up to about 70% theory.

While the more recent prior process was economically feasible and was a substantial improvement over the older process, it had numerous disadvantages which are overcome by the present process. In the prior process trichloroacetamidine concentrations were of necessity limited to about 11% by weight of the organic solvent employed. At higher concentrations a precipitate, trichloroacetamidine hydrochloride, which forms during the addition of trichloromethanesulfenyl chloride renders the reaction mixture so viscous that proper agitation is for all practical purposes impossible. This adversely affects overall productivity of the prior process. We have now found that by controlling the pH of the reaction mixture during addition and reaction of trichloromethanesulfenyl chloride, the formation of trichloroacetamidine hydrochloride is substantially eliminated. We can thus increase the weight ratio of trichloroacetamidine to organic solvent and provide an overall increase in productivity of about 50%.

In the prior process, the reaction mixture was free of added water during the reaction of trichloroacetamidine with trichloromethanesulfenyl chloride to avoid decomposition of the reactants. The only water added to the system resulted from the subsequent use of aqueous caustic to effect ring closure. This was due to the belief that the poor yields obtained in the process described in U.S. Pat. No. 3,260,725 were caused by decomposition of reactants and/or product due to the presence of water during the reaction. To limit such decomposition and improve yields added water was therefore excluded from the system until after completion of the reaction. We have now found that the deleterious effect of added water on yield and productivity is more than offset by controlling the pH of the reaction mixture and limiting the amount of water added to just that necessary to solubilize sodium chloride formed during the reaction.

It has also been found that an unexpected increase in yields may be obtained by carefully controlling the stoichiometry under which the reaction is conducted. In the prior process disclosed in U.S. Pat. Nos. 3,260,725 and 3,260,588 trichloroacetamidine hydrochloride and trichloromethanesulfenyl chloride were employed in substantially equimolar proportions, i.e., plus or minus about 0.5%. The precise ratio of reactants was not believed to be critical. In practice, however, and in the more recent process referred to above, it was found that yields of about 70% of theory (as opposed to 56% in the patents) could be obtained if a stoichiometric amount or a slight molar excess of trichloromethanesulfenyl chloride was employed. It has now been found that yields in excess of 90% of theory can be obtained by employing a defined molar excess of trichloroacetamidine in combination with pH control. This was highly unexpected in view of our prior experience and at present the rationale behind this unexpected increase in yield is not clear. It is suspected, however, that the excess trichloroacetamidine catalyzes ring closure and thus prevents loss of adduct which occurred in the prior process.

It has also been found that purity of trichloromethanesulfenyl chloride employed in the reaction has a marked effect on trichloroacetamidine conversion. Sulfur chlorides, notably $S_2Cl_2$, frequently found in commercially available trichloromethanesulfenyl chloride reduce product yield by about 2% for each 1% present. It is desirable, therefore, although not critical to the invention, to employ trichloromethanesulfenyl chloride of high purity with respect to sulfur chlorides as a starting reactant. But in the absence of such material, which is extremely costly under presently known processes, we have found that the adverse effect of the sulfur chlorides, which exist in presently available trichloromethanesulfenyl chloride, on yields can readily be overcome by factoring the excess of trichloroacetamidine upward in a defined ratio.

Whereas the prior processes were suitable only for batch processing, the present process may be practiced utilizing batch or continuous operation. An additional advantage of the present process is that by utilizing a continuous process it may be conducted at higher temperatures then could be employed in the prior process, eliminating the need for refrigeration.

SUMMARY OF THE INVENTION

The present process is thus an improvement in the process disclosed by Schroeder in U.S. Pat. Nos. 3,260,725 and 3,260,588 and in the more recent process wherein trichloroacetamidine is reacted with trichloromethanesulfenyl chloride in the presence of an inert immiscible organic solvent followed by ring closure in the presence of aqueous caustic.

In the process of this invention improved yields and productivity are obtained by reacting a trichloromethanesulfenyl chloride with a defined molar excess of trichloroacetamidine at temperatures of −10°C. to +50°C. while controlling the pH of the reaction mixture to a pH within the range of 5–10 and thereafter recovering 3-trichloromethyl-5-chloro-1,2,4-thiadiazole.

DETAILED DESCRIPTION

The reaction between trichloroacetamidine and trichloromethanesulfenyl chloride to produce 3-trichloromethyl-5-chloro-1,2,4-thiadiazole appears to be a complex set of reactions occurring simultaneously which may be represented as follows:

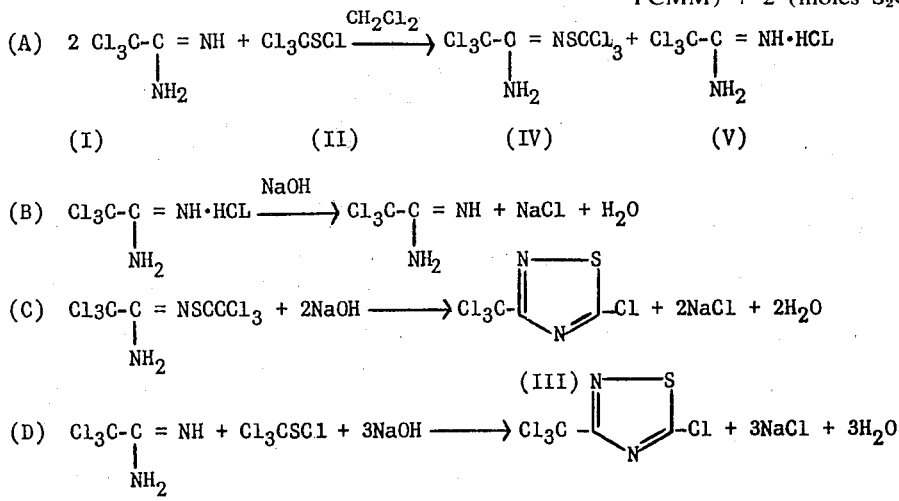

In the present process, it has been found that by carefully controlling reactant ratios, and by controlling the pH of the reaction mixture during the reaction of trichloroacetamidine (I) with trichloromethanesulfenyl chloride (II), also sometimes referred to as perchloromethyl mercaptan, an unexpected improvement in yields and productivity is obtained in the production of 3-trichloromethyl-5-chloro-1,2,4-thiadiazole (III).

Trichloroacetamidine is generally obtained by ammoniating trichloroacetonitrile which may be obtained by gas or liquid phase chlorination of acetonitrile. The preparation of trichloroacetamidine is thus well known to those skilled in the art.

In the present process, the use of a defined molar excess of trichloroacetamidine provides an unexpected increase in yields. As observed from the above reactions, trichloroacetamidine and trichloromethanesulfenyl chloride should combine on an equimolar basis in accordance with reaction D which summarizes the overall effect of reactions A-C. Unexpectedly, however, an excess of trichloroacetamidine is believed to catalyze ring closure shown in reactions C and D and prevent losses of the adduct or hydrochloride (V) which might otherwise occur.

The stoichiometric excess of (I) which is required for this purpose is about 1–7.5%, preferably 2–5%. Higher amounts may be utilized if desired but are commercially undesirable except as required due to the amount of sulfur chlorides, particularly $S_2Cl_2$, present in the trichloromethanesulfenyl chloride as discussed below.

Trichloromethanesulfenyl chloride (II) is prepared by chlorinating carbon disulfide and is readily available. It is preferable in the present process to utilize as a reactant a highly purified form of trichloromethanesulfenyl chloride of at least 98% purity and containing less than 1% sulfur chlorides, but commercially available forms containing from 1 up to about 8% $S_2Cl_2$ may also be employed by utilizing a slightly larger excess of trichloroacetamidine in the reaction mixture. It has been found that sulfur monochloride reacts with the amidine to form an adduct which is (1) not converted back to amidine and (2) is not cyclized to form the desired product. This by-product formation is readily compensated for by increasing the molar excess of trichloroacetamidine by about 2 moles for each mole of $S_2Cl_2$ present per mole of trichloromethanesulfenyl chloride employed. Thus the total molar excess of trichloroacetamidine required is an excess of 1–7.5% plus a factor to account for sulfur chlorides. This may conveniently be expressed by the following expression:

Molar Ratio TCAA/PCMM = (1.01 − 1.075) (moles PCMM) + 2 (moles $S_2Cl_2$ per mole PCMM) where TCAA represents trichloroacetamidine and PCMM represents trichloromethanesulfenyl chloride (perchloromethyl mercaptan). Since PCMM may contain from 0 up to about 0.08 moles sulfur monochloride per mole of PCMM, as little as 1.01 moles of TCAA may be required per mole of PCMM up to as much as about 1.20. This represents the minimum amounts necessary in the present invention. A larger excess of trichloroacetamidine may, of course, be employed if desired but no useful purpose will be served by increasing this amount to any great degree. Thus a suitable molar excess of trichloroacetamidine is one which is in the range of from about 1.01 to about 1.25 moles trichloroacetamidine per mole of trichloromethanesulfenyl chloride (a 1–25% excess), desirably 1.015 – 1.15 (a 1.5–15% excess) and preferably 1.02 to about 1.10 (a 2–10% excess), depending on the amount of sulfur chlorides present in the trichloromethanesulfenyl chloride.

The reaction of trichloroacetamidine with trichloromethanesulfenyl chloride is conducted in the presence of an inert immiscible organic solvent preferably in the presence of added water. Methylene chloride is the preferred organic solvent but other water immiscible organic solvents such as chloroform, trichloroethylene, benzene, toluene, and cyclohexane may also be employed. Suitably the weight ratio of trichloroacetamidine to organic solvent is from 1:1 to 1:5, preferably about 1:1 to 1:3.

Sufficient water to dissolve the water soluble salts formed during the reaction may be added prior to or simultaneously with addition of trichloromethanesulfenyl chloride and may be added either separately or with the base used to control pH. By dissolving all such salts, filtration of the reaction mixture prior to product workup is eliminated. The presence of added water in the reaction mixture also assists in avoiding the viscosity problem encountered when a high ratio of trichloroacetamidine to organic solvent is employed. It has been found that if the weight ratio of trichloroacetamidine to total added water is about 1:3 to 1:5, a subsequent filtration step may be eliminated. However, the present process may suitably be practiced using either considerably more or less water as desired. For example, a weight ratio of in excess of 1:5 up to about 1:7 may be used without a subsequent filtration step but yields are sacrificed somewhat. Above a ratio of about 1:7 yields may be significantly reduced as indicated above. Employing a weight ratio of less than about 1:3 makes a subsequent filtration step necessary but good yields may still be obtained even if no additional water is utilized. Accordingly, it is suitable to employ a weight ratio of trichloroacetamidine to total added water of about 1:0 to 1:7 preferably 1:3 to 1:5 and ideally about 1:3.5 to 1:4.5

It has been found that the control of pH during and the reaction in combination with the use of excess trichloroacetamidine is critical if high yields are to be obtained. It has been found that yields suffer if caustic addition is too fast, leading to an over-alkaline condition, or if it is withheld too long after trichloromethanesulfenyl chloride addition begins, leading to excess acidity due to the formation of HCl. Accordingly, it is desirable to control pH during the reaction to within a range of 5–10 preferably in the range of 7–9.5, by the gradual addition of a base selected from the group consisting of alkali metal hydroxides, bicarbonates, or carbonates. Preferably aqueous sodium hydroxide, sodium bicarbonate, sodium carbonate or a combination of these bases are employed to control pH. It has been noted that the pH may be slightly above or below the above ranges for short periods of time without substantially impairing yields. The permissible variation from this range and the time the variation may be permitted to exist has not been determined. It is desirable, therefore, to continuously monitor the pH and restore the system to the appropriate pH as rapidly as possible to minimize losses due to pH variations. It is also noted that if aqueous base is utilized this may also serve as a source of water to dissolve the salts formed during the reaction.

As indicated above, the improvements hereinabove described may be utilized in either a batch or continuous process. In conducting the reaction by a batch process trichloroacetamidine is preferably dissolved in a solvent comprising either an inert immiscible organic solvent or a mixture of organic solvent and water. If only the inert immiscible organic solvent is employed to dissolve trichloroacetamidine, additional water may then be added prior to or during addition of trichloromethanesulfenyl chloride. Alternatively, the desired amount of water may be added with the trichloromethanesulfenyl chloride or with the base or both. During the reaction it is necessary to maintain adequate agitation to assure that added trichloromethanesulfenyl chloride and base are well distributed in the reaction mixture. If sufficient agitation is not maintained the reaction may proceed too slowly and localized concentrations of base will contribute to reactant decomposition resulting in a loss of yields. Accordingly, it is desirable but not critical to have a sufficient amount of water present at all times to prevent the reaction mixture from becoming too viscous for proper agitation. The alternatives are to either increase the amount or rate of of water addition or to utilize equipment which will properly mix a more viscous reaction mixture.

It is preferred that the trichloromethanesulfenyl chloride be added slowly to the dissolved trichloroacetamidine. In a batch reaction system addition time (or reaction time which includes a suitable post addition hold time) adversely affects yields if the addition and/or reaction time is too long. It is desirable to add the required amount of trichloromethanesulfenyl chloride over a period of ¼ to 4 hours with sufficient agitation to effect proper distribution throughout the reaction mixture. Preferred addition time is ¼ to 3 hours and ideally ½ to 2 hours followed by a hold time of 15 minutes to 2 hours, preferably 30 minutes to 1 hour pH is controlled in the desired pH range by the providing base as needed the addition and post addition reaction period.

During the addition of PCMM temperature tends to rise due to exothermic heat of reaction. The temperature must therefore be controlled with cooling by any suitable means to a relatively low temperature suitably in the range of −20°C. to 30°C., preferably −10°C. to 20°C., and ideally between −5°C. and 10°C. This is particularly true in a batch reaction system where high concentrations of reactants and relatively long reaction times are employed. If higher temperatures are employed in the batch system, trichloromethanesulfenyl chloride addition times and post reaction hold times should be correspondingly reduced to avoid decomposition of reactants and/or product. On the other hand temperatures can be and preferably are higher if the reaction is conducted in a continuous reactor and may be as high as reflux temperature for the reaction mixture which is generally about 30°–50°C. Thus the continuous process reaction may be conducted at a temperature in the range of −20°C. up about 50°C. suitably 10°C. to 50°C. and preferably about 20°C. to about 50°C.

As trichloromethanesulfenyl chloride is added to and reacted with the trichloroacetamidine, the pH of the reaction mixture becomes acidic and the reaction cannot proceed to completion at a low pH. Accordingly, it is necessary to add a base as a hydrogen ion acceptor to drive the pH of the reaction mixture upward to a point at which the reaction will proceed to completion. If too much base is added or if it is added too soon, trichloroacetamidine and trichloromethanesulfenyl chloride will be attacked and degraded, detrimentally effecting yields. It is therefore essential that the pH of the reaction mixture be controlled during the addition and reaction of trichloromethanesulfenyl chloride.

In the batch reaction this may be accomplished either by the simultaneous addition of trichloromethanesulfenyl chloride and base or the incremental addition of small amounts of each to hold the pH to within the desired range. In a continuous process all ingredients are added simultaneously and continuously to maintain the pH of the reaction mixture in the range of 5–10, preferably 7–9.5 and product is continuously removed following a suitable reaction time which is determined by varying flow rate through the reactor.

Following completion of the reaction, any known means may be employed to recover 3-trichloromethyl-5-chloro-1,2,4-thiadiazole. It is preferred, however, to utilize substantially the same procedure used in the prior process. Assuming sufficient water is employed to avoid the necessity for a filtration step excess base is added to solubilize any remaining amidine in the aqueous layer. The methylene chloride layer is separated and washed preferably with an acid water wash (pH 3–5, HCl preferred) to remove any excess sodium salts or other impurities which may be present in the organic phase. The solvent is then evaporated and the product vacuum distilled if necessary to produce a product of the desired purity.

EXAMPLE I

This example demonstrates the prior process utilizing substantially stoichiometric amounts of reactants without pH control.

Trichloroacetamidine (63.9 g, 0.395 mole) was dissolved in 580 g. of methylene chloride and the solution was cooled to 0°C. Perchloromethyl mercaptan (76 g., 0.394 mole 96.4% containing 2.4% sulfur monochloride) was added over a two-hour period with the temperature held between 0°C. and 10°C. A solution of 63 g. of caustic in 250 g. of water was next added over a four-hour period at 10°-°C. The bottom product layer was phased, the pH adjusted to 5–6.5 and the volatiles stripped. The purity of the product in the residue was 83%. The residue was distilled to give 66 g. (70%) of product with a purity of 98%.

EXAMPLE II

This example demonstrates the effect of reducing addition time. The procedure was identical to that of Example I except that the PCMM was added over 1 hour and the caustic over 1½ hours. The purity after stripping of the solvents was 89.6%. The product was distilled to give 74 g. (79%) of product with a purity of 98%.

EXAMPLE III

This example shows the harmful effect that water exerts on the prior process.

Trichloroacetamidine (63 g., 0.395 mole) was dissolved in 130 g. of methylene chloride and the solution was cooled to 0°C. Water (500 g.) was added to the mixture. Perchloromethyl mercaptan (76 g., 96.4% pure, 0.394 mole) was added over a two-hour period with the temperature held between 0° and 10°C. Next a solution of 63 g. of caustic in 63 g. of water was added over a two-hour period.

The product was worked up by a procedure similar to that described in Example I to give 52.5 g. (65%) of product with a purity of 97%.

EXAMPLE IV

This example shows the yield improvement that results when the concentration of water is reduced so that just enough water to dissolve the sodium chloride is present.

The procedure was identical to Example III except that the amount of added water was reduced to 200 g. A yield of 67 g. (71%) was obtained.

EXAMPLE V

This example was run under the same conditions as Example IV except the PCMM was added over 90 minutes and the caustic added over 60 minutes. The purity of the crude product was 82%. The final yield was 74.2%. The product was/not distilled.

EXAMPLES VI–VIII

These examples were run essentially the same as Example V except that stoichiometry was varied by changing the ratio of trichloroacetamidine (Amidine) to perchloromethyl mercaptan (PCMM).

| Example | Amidine/PCMM Ratio | Product Purity Before Final Distillation | & Yield Based on PCMM |
|---|---|---|---|
| No. 6 | .95:1 | 82% | 75.7* |
| No. 7 | 1.02:1 | 78% | 81.4 |
| No. 8 | 1.05:1 | 90% | 84.7 |

*Based on amidine

EXAMPLES IX–X

These examples were run identically to runs No. 7 and No. 8 except that the perchloromethyl mercaptan purity was 98.5% and no sulfur chlorides were present in the mercaptan.

| Example | Amidine/PCMM Ratio | Product Purity Before Final Distillation | % Yield Based on PCMM |
|---|---|---|---|
| No. 9 | 1.02:1 | 91.5 | 87.7 |
| No. 10 | 1.05:1 | 94.1 | 89.5 |

EXAMPLES XI–XIII

These examples were run as in examples IX and X using pH control. The perchloromethyl mercaptan was added over 2 hours and the caustic was added as needed to control the pH between 7 and 9. After all the mercaptan was added the pH was raised to 12–13 and the product layer was phased. The product was washed with dilute acid and then the solvents were stripped. In Example XI, most of the water (200g) was added to the amidine and 50% caustic was used to control pH. In Example XII, 50 g. of water was added with the amidine and the rest with the caustic. In Example XIII, all the water was added with the caustic. The ratio for all runs was 1.05:1. The temperature was 8°–12°C.

| Example | Product Purity Before Final Distillation (Distillation Not Required) | % Yield Based on PCMM |
|---|---|---|
| No. 11 | 97.9 | 93.5 |
| No. 12 | 95.6 | 94.5 |
| No. 13 | 93.1 | 94.1 |

EXAMPLE XIV

This run shows the effect of running without pH control. The PCMM was added over 1 hours and then the caustic was added rapidly over 7 minutes and pH was very high during caustic addition. The yield was only 66.9% and the purity was 79–7% after stripping of volatiles.

What is claimed is:

1. In a process for preparing 3-trichloromethyl-5-chloro-1,2,4-thiadiazole wherein trichloroacetamidine or its hydrochloride is reacted with trichloromethanesulfenyl chloride in the presence of an inert immiscible organic solvent and the resulting adduct cyclized, the improvement which comprises:

reacting trichloromethanesulfenyl chloride with a 1 to 25% molar excess of trichloroacetamidine at a temperature in the range of −20°C. to 50°C. while adding a base selected from the group consisting of an alkali metal hydroxide, carbonate or bicarbonate at a rate sufficient to maintain the pH of the reaction mixture within the range of 5–10, said molar excess being at least as great as the value of the expression (1.01 − 1.075) (moles PCMM) + 2(moles $S_2Cl_2$ per mole PCMM) wherein PCMM represents trichloromethanesulfenyl chloride.

2. The process of claim 1 wherein the pH of said reaction mixture is maintained during said reaction at a pH in the range of 7–9.5.

3. The process of claim 2 wherein trichloromethanesulfenyl chloride containing not more than 1% $S_2Cl_2$ is utilized and said molar excess of trichloroacetamidine is in the range of 2–5%.

4. The process of claim 1 wherein said reaction is run continuously at a temperature in the range of 20°C. to 50°C.

5. The process of claim 1 wherein sufficient water is present to dissolve water soluble salts formed during the reaction.

6. The process of claim 5 wherein the weight ratio of trichloroacetamidine to total added water is 1:3 to 1:5.

7. The process of claim 6 wherein said water is added prior to or substantially simultaneously with addition of said trichloromethanesulfenyl chloride.

8. The process of claim 1 wherein said reaction is conducted as a batch reaction at a temperature in the range of −20°C. to 30°C.

9. The process of claim 8 wherein trichloromethanesulfenyl chloride is added to said trichloroacetamidine over a period of ¼ to 4 hours and wherein said base is added during said period at a rate sufficient to maintain pH of the reaction mixture in the range of 7–9.5.

10. The process of claim 9 wherein sufficient added water is present to dissolve water soluble salts formed during the reaction.

* * * * *